United States Patent [19]

Blacklock et al.

[11] Patent Number: 4,968,814
[45] Date of Patent: Nov. 6, 1990

[54] (S)-ALKYL 3-(THIEN-2-YLTHIO)BUTYRATE AND ANALOGS AND SYNTHESIS THEREOF

[75] Inventors: Thomas J. Blacklock, Clark; Edward J. J. Grabowski, Westfield; Paul Sohar, Warren, all of N.J.

[73] Assignee: Merck & Co., Inc., Rahway, N.J.

[21] Appl. No.: 510,806

[22] Filed: Apr. 18, 1990

[51] Int. Cl.$^5$ .......................................... C07D 333/32
[52] U.S. Cl. ...................................................... 549/66
[58] Field of Search ........................................... 549/66

[56] References Cited

U.S. PATENT DOCUMENTS 4,021,450  5/1977  Ahrens et al. ........................ 549/66
4,245,107  1/1981  Shibuya et al. ...................... 549/66
4,797,413  1/1989  Baldwin et al. ..................... 514/432

Primary Examiner—Alan Siegel
Attorney, Agent, or Firm—William H. Nicholson; Joseph F. DiPrima

[57] ABSTRACT (S)-Alkyl 3-(thien-2-ylthio)butyrate and analogs are intermediates in the synthesis of the chiral (S,S)-5,6-dihydro-4-ethylamino-6-methyl-4H-thieno[2,3-b]thiopyran-2-sulfonamide-7,7-dioxide and analogs thereof, topically effective carbonic anhydrase inhibitors useful in the treatment of ocular hypertension and glaucoma.

4 Claims, No Drawings

(S)-ALKYL 3-(THIEN-2-YLTHIO)BUTYRATE AND ANALOGS AND SYNTHESIS THEREOF

SUMMARY OF THE INVENTION

This invention is concerned with a novel chiral compound of structural formula I and asymmetric processes for its preparation.

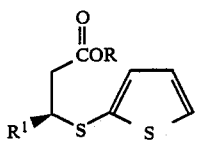
I

Compound I is a key intermediate in the synthesis of the compound of formula:

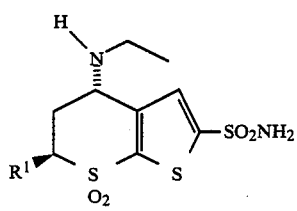

which is a carbonic anhydrase inhibitor topically effective in the treatment of ocular hypertension and glaucoma.

The process for preparing Compound I comprises treating a nucleophile of structure II with a compound of structure III as shown:

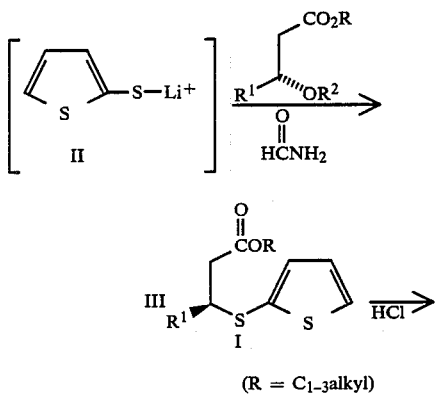

(R = $C_{1-3}$alkyl)

wherein the R groups are as hereinafter defined.

BACKGROUND OF THE INVENTION

The carbonic anhydrase inhibitor described above is disclosed in U.S. Pat. No. 4,797,413 which also discloses a process for preparing the racemic modification of the alkyl 3-(thien-2-ylthio)butyrate and its homologs. The prior art process comprises addition of the 2-thienyl-thiol across the double bond of a substituted acrylic acid:

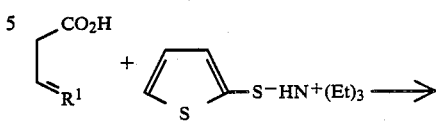

followed by synthesis of the final diastereomeric product, the isomers of which must be separated and each resolved to obtain the most active (S,S)-enantiomer. The isomer separations result in an automatic loss of the bulk of the chemical product.

It is therefore an object of this invention to provide a chiral intermediate for the synthesis of a chiral final product more economically than previously possible.

It is also an object of this invention to provide a process for the synthesis of the chiral intermediate.

DETAILED DESCRIPTION OF THE INVENTION

The novel compound of this invention has structural formula I.

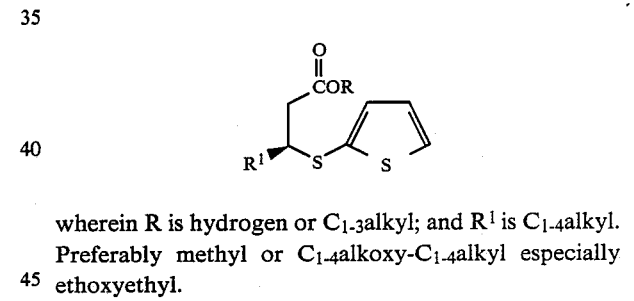

wherein R is hydrogen or $C_{1-3}$alkyl; and $R^1$ is $C_{1-4}$alkyl. Preferably methyl or $C_{1-4}$alkoxy-$C_{1-4}$alkyl especially ethoxyethyl.

The novel process of this invention comprises the condensation of thienyl-2-thiol with a chiral $C_{4-7}$ alkanoate having a leaving group in the 3-position and may be represented as follows:

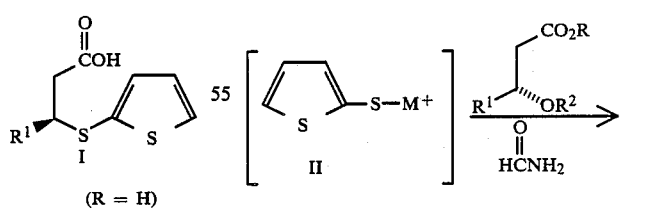

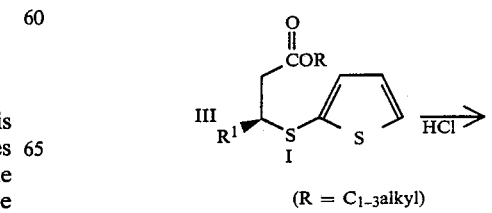

(R = $C_{1-3}$alkyl)

-continued

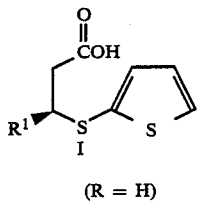

(R = H)

wherein; $R^2$ is mesyl, tosyl, p-methoxybenzesulfonyl, benzenesulfonyl, m- or p-chlorobenzenesulfonyl or p-nitrobenzenesulfonyl and $M^+$ is $(C_2H_5)_3NH^+$ or $Li^+$.

The condensation is conducted in formamide or in an ethereal solvent such as THF, diethyl ether or 1,2-dimethoxyethane in the presence of formamide, at about 10°–40° C., preferably about 20°–25° C. until the reaction is substantially complete or about 10–55 hours.

Experimental

NMR Spectra were recorded on a Varian XL-300 or Brucker AM-250 spectrometer in $CDCl_3$ or $D_6$-DMSO referenced to tetramethylsilane (TMS) at 0.0 ppm. FTIR Spectra were obtained on a Nicolet 7199 spectrophotometer. Melting points were recorded on a Thomas Hoover capillary melting point apparatus. UV Spectra were obtained on a Cary 210 spectrophotometer. Specific rotations were recorded on a Perkin Elmer 241 polarimeter. Thin layer chromatography (TLC) plates used were Whatman MK6F Silica Gel (1×3").

Methyl (R)-3-(p-Toluenesulfonyloxy)butyrate.

To a 22-L three-necked round-bottomed flask affixed with an overhead mechanical stirrer, thermocouple, nitrogen bubbler, and provision for external cooling was charged dry pyridine (3.0 L, K.F. <0.005%) and methyl (R)-3-hydroxybutyrate (1.14 assay Kg, 9.67 moles, K.F. <0.005 wt %). While maintaining the temperature at < −5° C., p-toluenesulfonyl chloride (2.35 Kg, 98% tech. grade, 12.4 mole) was added to the alcohol/pyridine mixture. (The charge of tosyl chloride should be at least 125 mole % of the alcohol charge and should be adjusted upward, mole for mole, to compensate for the total system water content.) The reaction mixture was stirred for 24 hours at 0° C. or until judged complete by HPLC. Workup commenced by cooling the batch to −16° C. and subsequently adding water (200 mL), dropwise, while maintaining the temperature at <2° C. (It is essential that all tosyl chloride be decomposed with the addition of water while the batch is still homogeneous. If too much water is added initially, the reaction becomes biphasic and the rate of hydrolysis slows dramatically. Tosyl chloride then co-crystallizes with the product.) The batch was then aged with vigorous agitation for 30 minutes at 0°–2° C. An additional 400 mL of water was then added in similar fashion. After 30 minutes, HPLC analysis (see below) showed no remaining tosyl chloride. The batch was then diluted with the slow addition of water (9 L) at 0°–5° C. Product crystallizes spontaneously. After a 2 hour age at 0°–5° C. the batch was filtered, the product cake slurry-washed with water at least five times to remove p-toluenesulfonic acid and pyridine, and sucked dry under nitrogen to constant weight. The yield of methyl (R)-3-(p-toluenesulfonyloxy) butyrate was 2.57 Kg (98%), mp 46°–47.5° C. HPLC Conditions: [Sample preparation: A quantity of 0.1 mL of the above reaction mixture was shaken with 5 mL water, 5 mL ethyl acetate, and 0.1 mL concentrated hydrochloric acid to neutralize and remove the pyridine solvent. The mixture was then separated and the upper ethyl acetate layer diluted 1:10 with acetonitrile for injection. At 254 nm, an area ratio of 1:2 product tosylate:tosyl chloride signifies a complete reaction. Column: C-8 Altex Ultra sphere 5 micron (4.1 mm×25 cm); Eluant: 50:50 A:B isocratic @2.0 mL/min, A=$H_2O$ (0.1% $H_3PO_4$ v/v), B=$CH_3CN$; Temp: 24° C.; Detector: UV@254 nm; $R_T$ tosylate (1) 3.5 min., $R_T$ tosyl chloride 5.5 min.]. Analysis: $^1H$ NMR ($CDCl_3$) 7.79(d,2H,J=8.36 Hz), 7.34(d,2H,J=8.36 Hz), 4.97(m,1H), 3.59(s, 3H), 2.74(dd,1H,J=15.8,J=6.5 Hz), 2.52(dd,1H,J=15.8,J=6.8 Hz), 2.45(s,3H), 1.36(d,3H,J=6.3 Hz); $^{13}C$ NMR ($CDCl_3$) 169.7(s), 144.8(s), 133.9(s), 129.8(s), 127.7(s), 75.8(s), 51.8(s), 41.2(s), 21.6(s), 20.9(s); $[\alpha]_{405}^{25}$=−16.3 (c=2,toluene); Anal. Calcd. for $C_{12}H_{16}O_5S$: C,52.94; H,5.88; S,11.76. Found: C,52.98; H,5.93; S,11.76.

Methyl (S)-3-(2-Thienylthio)butyrate.

Thiophene (18.1 mL, 19.0 g, 226 mmol) and anhydrous THF (200 mL, K.F. <0.05%) were charged to a 1-L three-necked round-bottomed flask fitted with a thermometer, mechanical stirrer, nitrogen bubbler, and addition funnel. The solution was cooled to −5° C. and n-butyl lithium (137 mL of 1.6 M in hexane, 219 mmol) was added at such a rate as to maintain the temperature at <0° C. After addition was complete the reaction was stirred for 1 h at 0°–5° C. To the rapidly stirred 2-lithiothiophene solution was added powdered sulfur (7 g, 219 mmol), portionwise, while maintaining the temperature at <5° C. After addition of the sulfur the reaction mixture was stirred for 2.5 h at 0°–5° C. Cooling was maintained and the reaction mixture was diluted with formamide (200 mL tech. grade) that had been thoroughly purged with nitrogen. To this biphasic mixture was then added solid methyl (R)-3-(p-toluenesulfonyloxy) butyrate (57.0 g, 209 mmol) and the mixture was stirred at 25° C. for three days. (The progress of the alkylation was conveniently monitored by hplc: Column: C-8 Altex Ultrasphere 5 micron (4.1 mm×25 cm); Gradient: 65:35 A:B@2.0 mL/min to 20:80 over 20 min., A=$H_2O$ (0.1% $H_3PO_4$ v/v), B=$CH_3CN$; Temp: 45° C.; Detector: UV@230 nm; $R_T$Methyl (S) 3 (2-thienylthio) butyrate 12.50 min. The entire reaction mixture was then poured into a stirred vessel containing water (400 mL) and ethyl acetate (200 mL) at 25° C. The organic layer was separated and the aqueous layer was back extracted once with 1:1 ethyl acetate:hexanes (100 mL). The organic layers were combined and washed with brine (200 mL). Concentration of the ethyl acetate solution from water under vacuum removed residual ethyl acetate and afforded a viscous oil/water mixture (ca. 100 mL water/60 mL oil) which was hydrolyzed directly in the next step. A small sample of the oil was chromatographed on silica gel (10% ethyl acetate in hexanes) for byproduct identification and product characterization and chirality determination.

The first eluted component, $R_f$=0.82, was identified as 2-thiophene disulfide on the basis of its spectral characteristics. Analysis: $^1H$ NMR ($CDCl_3$) 7.35(m,2H), 7.23(m,2H), 6.97(m,2H),; $^{13}C$ NMR ($CDCl_3$) 135.5(s), 132 8(s), 129.7(s), 127.5(s); HRMS Calcd. for $C_8H_6S_4$ (M+) 229.9352. Found: 229.9353.

The product eluted as the major second fraction, $R_f$=0.52, was identified as methyl (S)-3-(2-thienylthio)-butyrate on the basis of its spectral characteristics.

Analysis: $^1H$ NMR (CDCl$_3$) 7.41(m,1H), 7.17(m,1H), 7.02(m,1H), 3.69(s,3H), 3.39(m,1H), 2.67(dd,1H,J=15.7,J=6.4 Hz), 2.42(dd,1H,J=15.7,J=8.2 Hz), 1.32(d,3H,J=6.9 Hz); $^{13}C$ NMR (CDCl$_3$) 171.6(s), 136.2(s), 130.9(s), 130.7(s), 127.7(s), 51.7(s), 41.8(s), 41.4(s), 20.7(s); Anal. Calcd. for C$_9$H$_{12}$O$_2$S: C,50.00; H,5.56; S,29.63. Found: C,50.08; H,5.65;. Chirality: >98:2 S:R by NMR using (+)-Eu(hfc)$_3$ chiral shift reagent and monitoring the methyl doublet at 1.32 ppm.

The third eluted component, R$_f$=0.42, was identified as methyl (S)- 3-[5-(thienyl- 2-thio)-thienyl-2-thio]butyrate on the basis of its spectral characteristics. Analysis: $^1H$ NMR (CDCl$_3$) 7.39(m,1H), 7.25(m,1H), 6.99(m,1H), 3.67(s,3H), 3.39(m,1H), 2.65(dd,1H,J=15.7,J=6.5 Hz), 2.43(dd,1H,J=15.7,J=8.0 Hz), 1.31(d,3H,J=6.8 Hz); $^{13}C$ NMR (CDCl$_3$) 171.5(s), 140.7(s), 136.3(s), 134.5(s), 133.8(s), 133.8(s), 131.7(s), 130.4(s), 127.6(s), 51.8(s), 42.0(s), 41.4(s), 20.8(s); HRMS calcd. for C$_{13}$H$_{14}$O$_2$S$_4$ (M+) 329.9877, Found: 329.9872.

(S)-3-(2-Thienylthio)butyric Acid

To the viscous oil/water mixture of methyl ester above was added concentrated hydrochloric acid (100 mL, 12N). The mixture was brought to reflux (110° C.) with vigorous agitation for three hours, or until complete, as Judged by HPLC. (The constant boiling mixture of HCl/water is approximately 6.5 N.) The product was extracted twice into toluene (160 mL for the first extraction and 50 mL for the second extraction). The combined toluene extracts were washed with brine and dried azeotropically under vacuum at 50° C. bath temperature to a volume of 200 mL containing approximately 45 g product at K.F. <0.05%. A small portion of the product was chromatographed on silica gel for product characterization.

$^1$H NMR (CDCl$_3$) 7.42 (M,1H), 7.19 (M,1H), 7.03 (M,1H), 3.38 (M,1H), 2.72 (dd, 1H, J=16.0, J=6.4 Hz), 2.48 (dd, 1H, J=16.0, J=8.0 Hz), 1.35 (d, 3H, J=6.8 Hz);

$^{13}$NMR (CDCl$_3$) 177.5(s), 136.4(s), 130.9(s), 130.6(s), 127.7(s), 41.4(s), 41.3(s), 20.6(s);

HRMS calcd. for C$_8$H$_{10}$O$_2$S$_2$ (M+) 202.0122, Found 202.0121

Employing the procedures substantially as described in the foregoing experimental but substituting for the methyl (R)-3-hydroxybutyrate used therein comparable amounts of the 3-hydroxy esters shown in the following table, there are produced the (S)-3-(2-thienylthio)alkanoic acids also described in the following table:

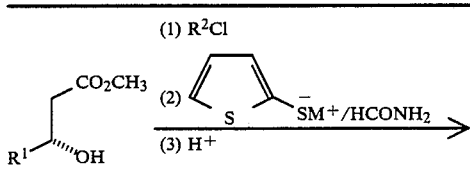

-continued

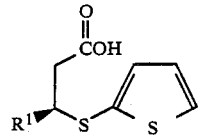

| R$^1$ |
|---|
| CH$_3$O(CH$_2$)$_2$— |
| C$_2$H$_5$O(CH$_2$)$_2$— |
| C$_3$H$_7$O(CH$_2$)$_2$— |
| CH$_3$O(CH$_2$)$_3$— |
| C$_2$H$_5$O(CH$_2$)$_2$— |
| C$_2$H$_5$O(CH$_2$)$_3$— |
| C$_4$H$_9$O(CH$_2$)$_2$— |
| CH$_3$O(CH$_2$)$_4$— |
| C$_2$H$_5$— |
| C$_3$H$_7$— |

What is claimed is:

1. A process for the preparation of a compound of structural formula I:

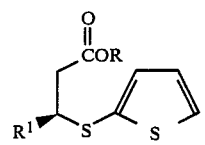

wherein R is hydrogen or C$_{1-3}$alkyl; and R$^1$ is C$_{1-4}$alkyl or C$_{1-4}$alkoxy-C$_{1-4}$alkyl; which comprises treating a compound of structural formula II:

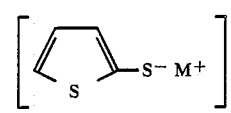

wherein M+ is (C$_2$H$_5$)$_3$NH+ or Li+ with a compound of structural formula III:

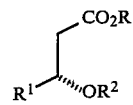

wherein R is C$_{1-4}$alkyl, R$^2$ is tosyl, mesyl benzenesulfonyl, p-methoxybenzenesulfonyl, p- or m-chlorobenzenesulfonyl or p-nitrobenzenesulfonyl in formamide or a mixture of an ethereal solvent and formamide at a temperature of about 10° to 40° C. for about 10–55 hours to produce Compound I (R=C$_{1-3}$alkyl) followed by deesterification to produce Compound I (R=H).

2. The process of claim 1 wherein the ethereal solvent is formamide and the temperature is 20°–25° C.

3. The process of claim 1 wherein R and R$^1$ are methyl, R$^2$ is tosyl and M+ is (C$_2$H$_5$)$_3$NH+ or Li+.

4. The process of claim 2 wherein R and R$^1$ are methyl, R$^2$ is tosyl and M+ is (C$_2$H$_5$)$_3$NH+ or Li+.

* * * * *

UNITED STATES PATENT AND TRADEMARK OFFICE
CERTIFICATE OF CORRECTION

PATENT NO. : 4,968,814

DATED : November 6, 1990

INVENTOR(S) : Blacklock et al

It is certified that error appears in the above-identified patent and that said Letters Patent is hereby corrected as shown below:

In column 6, line 56, "formamide" should read ---THF---.

Signed and Sealed this

Nineteenth Day of May, 1992

Attest:

DOUGLAS B. COMER

Attesting Officer     Acting Commissioner of Patents and Trademarks